(12) United States Patent
Fernandez

(10) Patent No.: US 7,519,622 B2
(45) Date of Patent: Apr. 14, 2009

(54) SYSTEM AND METHOD FOR COLLECTING DATA FROM DATA SOURCES USING DATA COLLECTION TOOLS

(75) Inventor: Ronald E. Fernandez, Ann Arbor, MI (US)

(73) Assignee: Unival, Inc., Ann Arbor, MI (US)

( * ) Notice: Subject to any disclaimer, the term of this patent is extended or adjusted under 35 U.S.C. 154(b) by 330 days.

(21) Appl. No.: 10/989,989

(22) Filed: Nov. 16, 2004

(65) Prior Publication Data

US 2006/0106787 A1   May 18, 2006

(51) Int. Cl.
*G06F 17/30* (2006.01)
*G06F 17/00* (2006.01)
*G06F 19/00* (2006.01)

(52) U.S. Cl. .......................... 707/200; 707/102; 705/2; 705/4

(58) Field of Classification Search ........................ None
See application file for complete search history.

(56) References Cited

U.S. PATENT DOCUMENTS

| | | | | |
|---|---|---|---|---|
| 5,475,742 A | | 12/1995 | Gilbert | |
| 5,745,681 A | * | 4/1998 | Levine et al. | 709/200 |
| 5,924,074 A | * | 7/1999 | Evans | 705/3 |
| 5,950,010 A | * | 9/1999 | Hesse et al. | 717/178 |
| 6,006,230 A | * | 12/1999 | Ludwig et al. | 707/10 |
| 6,163,276 A | | 12/2000 | Irving et al. | |
| 6,460,041 B2 | * | 10/2002 | Lloyd | 707/10 |
| 6,691,116 B1 | | 2/2004 | Bart | |
| 6,751,650 B1 | * | 6/2004 | Finch et al. | 709/203 |
| 2002/0194314 A1 | * | 12/2002 | Kouznetsov et al. | 709/220 |
| 2004/0153338 A1 | * | 8/2004 | Kim et al. | 705/2 |

* cited by examiner

*Primary Examiner*—John E Breene
*Assistant Examiner*—Aleksandr Kerzhner
(74) *Attorney, Agent, or Firm*—Brinks Hofer Gilson & Lione

(57) ABSTRACT

A system and a method for collecting data from a data source that includes a database containing a tool for collecting data from the data source and creating a data record, a tool selector in communication with the database for selecting the tool from the database, a tool processor for executing the tool, and a communication channel for communicating between the database and the tool processor. The tool is selected from the database by the tool selector and transmitted via the communication channel to the tool processor for use by the operator in creating a data record that is transmitted to the database via the communication channel.

15 Claims, 3 Drawing Sheets

SYSTEM AND METHOD FOR COLLECTING DATA FROM DATA SOURCES USING DATA COLLECTION TOOLS

TECHNICAL FIELD

This invention relates generally to the field of data collection, and more specifically to a new and useful system and method for collecting data from data sources using data collection tools.

BACKGROUND

Specific information relevant to the health of a patient may be stored in files, records, and other data sources located in many different medical facilities such as physician offices, hospitals, skilled nursing facilities, medical laboratories and free standing radiology clinics. Patient information is often required by organizations authorized to receive such information such as medical service provider plans, governmental agencies, including Medicare and Medicaid, and other authorized organizations. The specific information may be found in many locations, on various media, in numerous formats and amid a considerable amount of non-relevant data. For example, data collection may take the form of extracting data from electronic or paper files and records or collecting data visually by inspection during an on-site audit of a medical facility. Collecting, abstracting, and organizing the relevant data into a format that is readily analyzed by the resources of a medical service provider plan is a complex and time consuming task. Thus, authorized organizations have a need for new and efficient systems and methods for collecting, abstracting and organizing specific medical information from the files of their participating medical service providers.

SUMMARY

In one aspect of the invention, a system is provided for collecting data from a data source and creating data records that includes a database containing tools for collecting the data from the data sources and creating a data records. A tool selector in communication with the database is also provided for selecting a tool from the database and a tool processor for executing the tool. A communication channel communicates between the database and the tool processor enabling a tool to be selected by tool selector program running on an application processor and transmitted to the tool processor for use in creating a data record which is transmitted to the database via the communication channel.

In another aspect of the invention, a method is described in which a tool is selected from a database, transmitted from the database to a tool processor by way of a communication channel for use by an operator to facilitate the collection of data from a data source and the creation of a data record that is transmitted from the tool processor to the database via the communication channel.

These and other aspects and advantages of the present invention will become apparent upon reading the following detailed description of the invention in combination with the accompanying-drawings.

DESCRIPTION OF THE PREFERRED EMBODIMENT

The following description of the preferred embodiment of the invention is not intended to limit the invention to this preferred embodiment, but rather to enable any person skilled in the art of data collection to make and use this invention.

Figure 1:
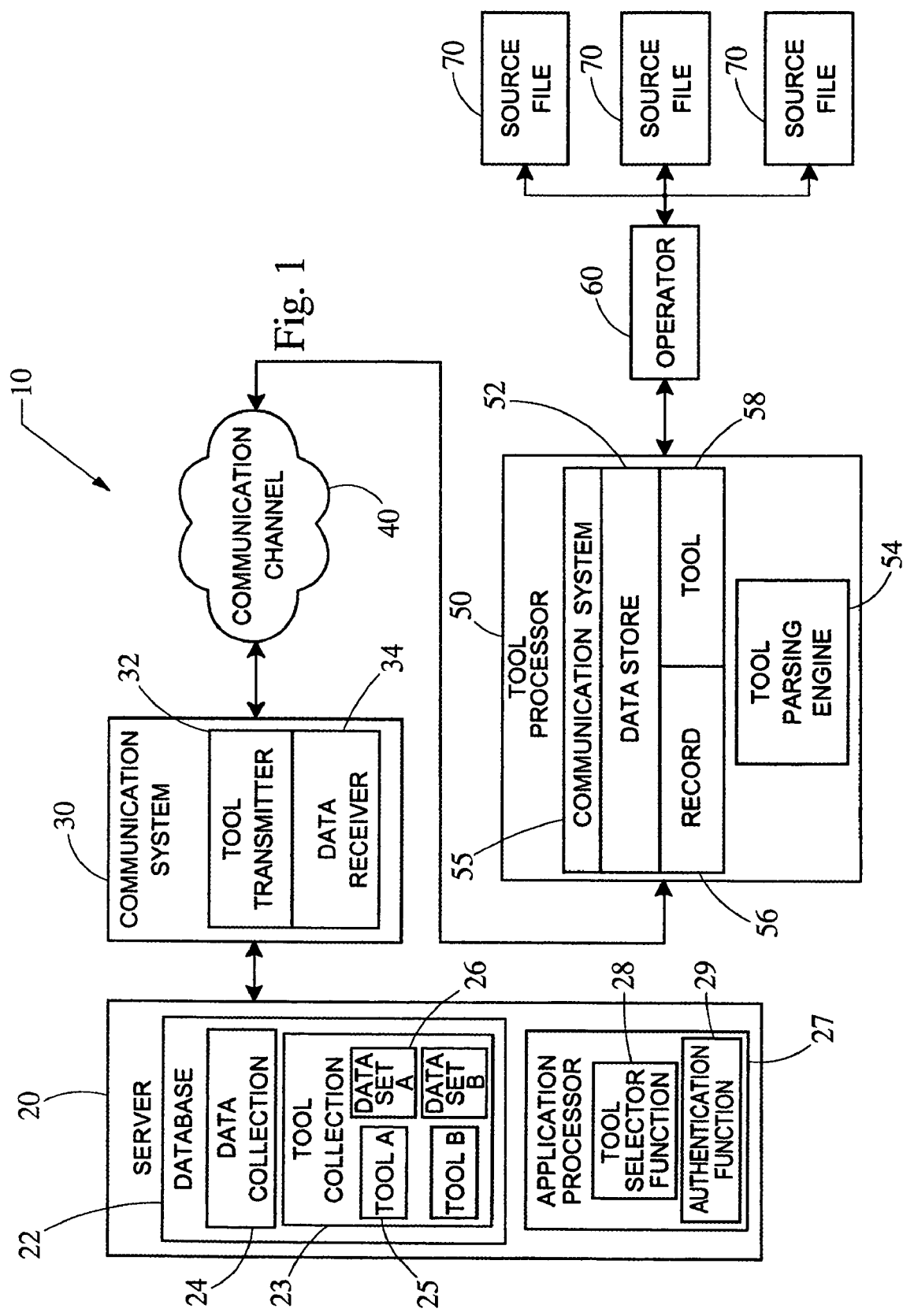
FIG. 1 is a block diagram showing the architecture and functional entities of the invention.

As shown in FIG. 1, the preferred embodiment of the system 10 for collecting data from a data source includes a server 20 linked to a communication system 30. The server 20 contains a database 22 in communication with an application processor 27. The application processor 27 has a tool selector functionality 28 for selecting tools appropriate for a given data collection assignment and an authentication functionality 29 to identify operators 60 of tool processors 50 to enable the particular data collection assignments that have been assigned to the operators 60 to be correlated.

The application processor 27 may be resident on the same physical machine or server 20 as the database 22 or could be physically separated from the database 22 and residing on a separate machine. The database 22 contains a data collection 24 and a tool collection 23. The tool collection 23 contains at least one data tool 25 but could contain a suite of diverse data tools 25 for collecting data, each data tool 25 being linked or associated with a data set 26. Each data set 26 contains parameters and other information and data that are useful in the execution of the associated or linked data tool 25.

The communication system 30, which contains a tool transmitter 32 for transmitting the data tools 25 and data sets 26 to the tool processor 50 and a data receiver 34 for receiving data records created by the operator 60 based on information contained in the source files 70, which are stored in the data collection 24 residing on the server 20. The communication system 30 communicates through a communication channel 40 with the tool processor 50. The tool processor 50 is comprised of a data store 52, which stores data records 56 and data tools 58. Also included within the tool processor 50 is a tool parsing engine 54 for parsing and executing instructions that form the code or script of the data tools 25 and a local communication system 55 for establishing communication between the operator 60 and the application processor 27 through the communication channel 40. The communication channel 40 and the other links between the various components of the system 10 may be dedicated facilities, a Wide Area Network (WAN), a Virtual Private Network (VPN), a local area network, the internet or an number of other land based, terrestrial based or wireless communication facilities, networks or resources.

The tool processor 50 is utilized by an operator 60 that has access to source files 70. The tool processor 50 may be a PDA, workstation, laptop computer, desktop computer or any other of various platforms containing processing units capable of executing the data tool to create data records. In the preferred embodiment, the operator 60 is a human agent who may be assigned to read through source files 70 that are paper and/or electronic files in a physician's office, hospital, skilled nursing facility, medical laboratory, free standing radiology clinic or at any other location or facility of an entity that participates in the medical service provider plan. The specific information or data that the operator 60 is assigned to collect may be found in source files 70 that are of various media and in numerous formats. The sources files 70 from which the operator 60 may extract the information or data may be electronic or paper files and records or the operator may collect the data or information source files 70 that are the physical locations or facilities themselves by inspecting or auditing the premises.

Figure 2:
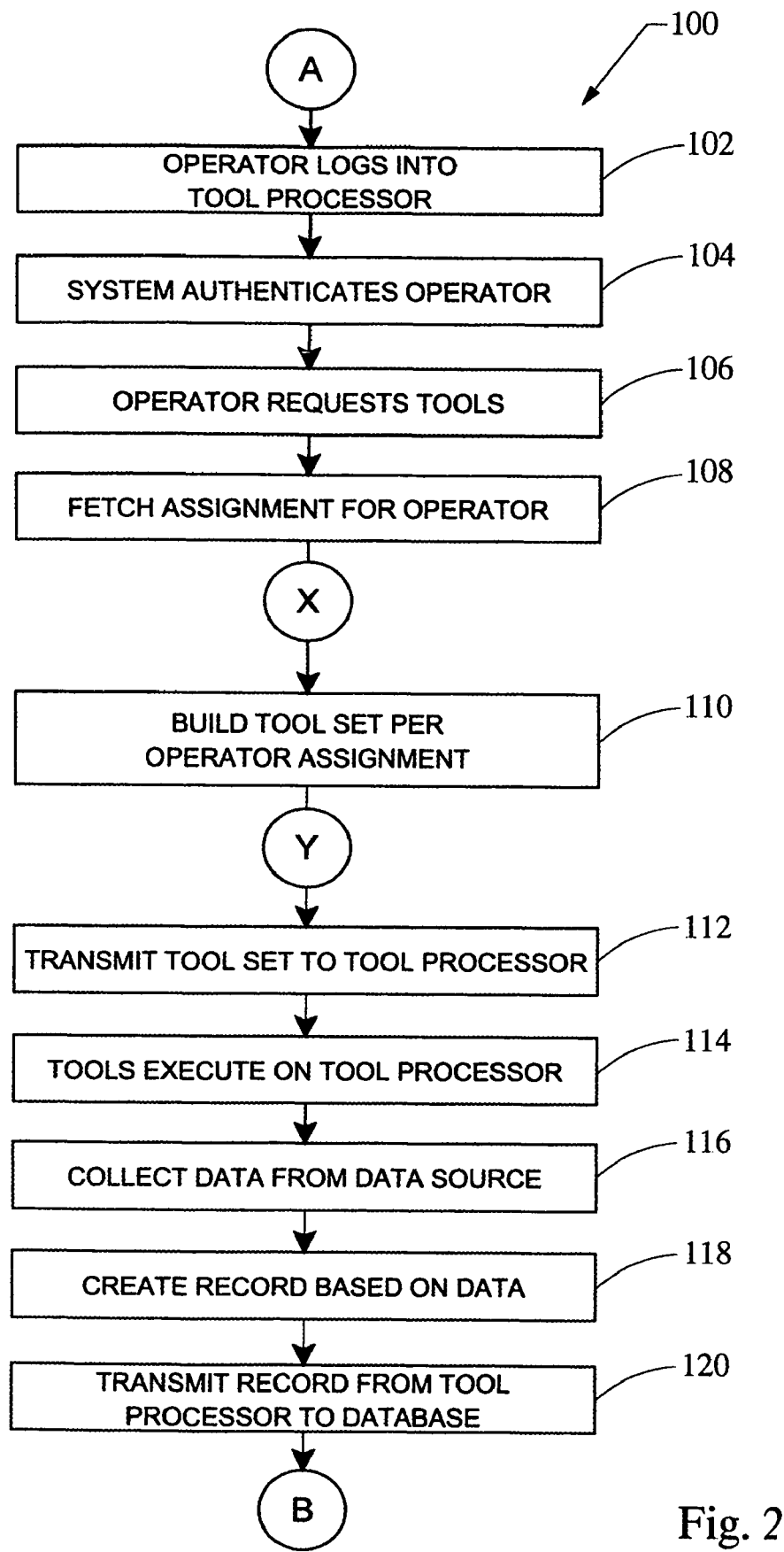
FIG. 2 is a flow chart showing the process flow of the invention.

Referring now to FIG. 2, the method for collecting data from a data source 100 begins in step 102 when the operator 60 logs onto an application program. The application program may reside on the tool processor 50 or may be resident on the remote application processor 27. The application program authenticates the operator in step 104 allowing the operator in step 106 to request the appropriate tools for a particular data collection assignment. In step 108 the application program fetches the assignment for the operator 60 and begins in step 110 to build a tool set that will enable the operator 60 to collect the information or data of interest to the organization that has been authorized to receive the patient's information, such as a medical service provider plan.

In step 112, the tool set is transmitted by the tool transmitter 32 within communication system 30 from the tool collection 23 within the database 22 to the tool processor 50 via the communication channel 40. The tool set is stored in the tool store 58 within the data store 52 resident on the tool processor 50. The tools are executed by the tool parsing engine 54 within the tool processor 50 in step 114 enabling the operator 60 create data records 56 in step 118 from the relevant data collected from the source files 70. The data records 56 are stored within the data store 52 of tool processor 50. The record store 56 and the tool store 58 resident on tool processor 50 may be contained with the same or different devices.

In step 120, the data record or records 56 are transmitted from the tool processor 50 through its communication system 55 via the communication channel 40 to the data receiver 34 to a remote communication system 30 that provides a communication interface for the server 20. The data records 56 are stored in the data collection 24 residing on the server 20.

Figure 3:
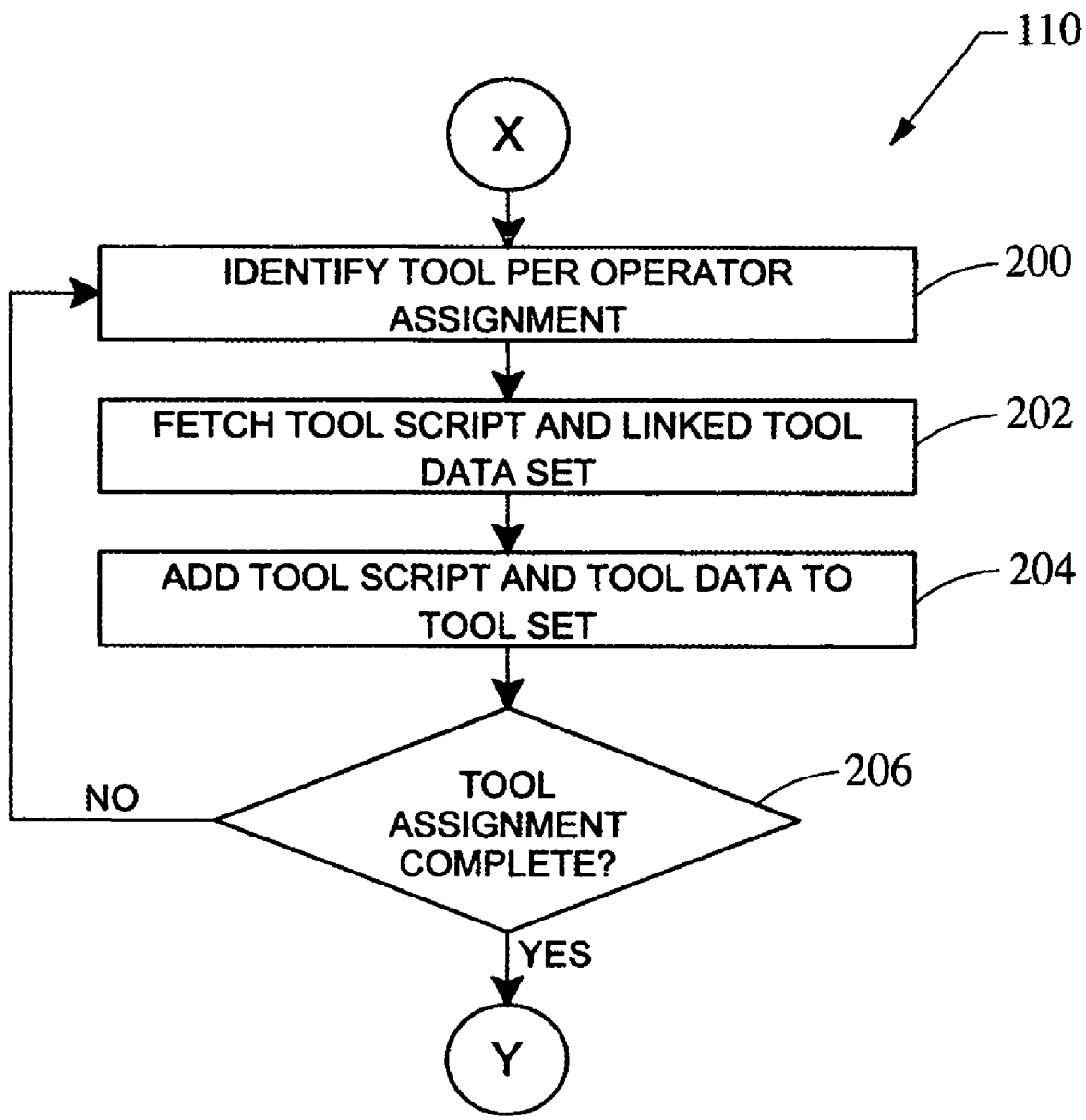
FIG. 3 is a flow chart showing the process flow for building a tool set.

The process of building the tool set for the operator's assignment in step 110 is outlined in more detail in FIG. 3 beginning in step 200 in which the application program identifies a tool 25 that is needed for the operator 60 to perform his or her assignment. The application program fetches the tool 25 script in step 202 and the data set 26 that is linked or associated with the identified tool 25 script. In step 204 the fetched tool 25 script and data set 26 are added to a tool set for the operator's 60 assignment.

In step 206, the application program decides whether or not all of the tools 25 and linked or associated data sets 26 that are required for the operator 60 to compete the assignment have been accumulated in the tool set and returns to step 200 if all of the tools 25 and linked or associated data sets 26 have not been accumulated to complete the assignment. If all of the tools 25 and linked or associated data sets 26 required by the operator to complete the assignment have been accumulated the process continues to step 112 in which the tool set is transmitted via the communication channel 40 to the communication system 55 in the tool processor 50 as described above.

The foregoing description of the preferred embodiment is not intended to limit the invention to this preferred embodiment, but rather to enable any person skilled in the art of data collection to make and use this invention. As any person skilled in the art of data collection will recognize from the foregoing description and from the figures and claims, modifications and changes can be made to this preferred embodiment of the invention without departing from the scope of this invention defined in the following claims.

I claim:

1. A system to facilitate a human operator's extraction of specific health data of interest to a medical service provider plan from a data source of a healthcare service provider comprising:
   a computer storing a database containing at least one collection of data collection tools to instruct said human operator to extract said specific health data for at least one patient from said data source of said healthcare service provider to create a data record in a format that is analyzed by said medical plan provider, said collection of tools being a suite of diverse data tools each suitable to be included in building a data collection assignment used by said human operator to extract said specific health data from said data source of said healthcare service provider;
   a tool selector in communication with said database, said tool selector selecting said at least one tool from said tool collection contained in said database, said at least one tool being a tool included in said data collection assignment for said human operator to extract said specific health data of interest to a medical service provider plan from said data source of a healthcare service provider;
   a tool processor executing said at least one tool contained in said data collection assignment to instruct said human operator to extract said specific health data from said data source of said healthcare service provider to create said record in a format that is analyzed by said medical plan provider; and
   a communication channel communicating between said database and said tool processor;
   wherein said at least one tool is selected from said suite of diverse data tools contained in said collection of tools from database by said tool selector to build a data collection assignment and transmitted to said tool processor, said data collection assignment used by said human operator collecting a subset of said specific health data from said data source of a healthcare service provider and in creating said data record organized into a format analyzable by a medical service provider plan that is transmitted to said database via said communication channel.

2. The system of claim 1, further comprising:
   a communication system, in communication with said database and said tool processor, said communication system transmitting said at least one tool from said database to said tool processor and receiving said data record from said tool processor.

3. The system of claim 1, further comprising:
   a data store within said tool processor storing said data record in said format that is analyzed by a medical plan provider.

4. The system of claim 1, further comprising:
   a tool parsing engine within said tool processor, said tool parsing engine parsing instructions of said at least one tool appropriate for said data collection assignment to extract said specific health data.

5. The system of claim 1, further comprising:
   an application processor in communication with said database, said application processor having a tool selector that selects at least one tool appropriate for said data collection assignment to extract said specific health data from said database.

6. The system of claim 1, further comprising:
   a data set associated with said at least one tool, said data set containing parameters useful in the execution of said at least one tool selected for inclusion in said data collection assignment to extract said specific health data.

7. The system of claim 2, wherein said communication system contains a tool transmitter that transmits to said tool processor said at least one tool that is selected for inclusion in said data collection assignment to extract said specific health data.

8. The system of claim 2, wherein said communication system contains a data receiver that receives said data record in a format adapted for analysis by a medical plan provider from said tool processor.

9. The system of claim 5, wherein said application processor contains an authentication function that identifies at least one human operator of said tool processor and determines a particular tool set representing a particular data collection assignment to be assembled by said at least one human operator.

10. A method to facilitate a human operator's extraction of health data of interest to an authorized recipient from a data source of a healthcare service provider comprising the steps of:
   containing in a database stored on a computer at least one collection of data tools to instruct said human operator to extract said specific health data for at least one patient from said data source of a health care service provider to create a record in a particular format that is analyzed by a medical plan provider;
   selecting from a selector said at least one tool from said collection of data tools contained in said database, said at least one tool being a tool appropriate for said human operator to collect said health data for at least one patient from said data source of a healthcare service provider;
   executing said at least one tool on a processor;
   transmitting said at least one tool from said database to said processor using a transmitter;
   communicating between said database and said processor via a communication processor;
   selecting from said database said at least one tool collect said health data from said data source of a healthcare service provider;
   transmitting said at least one tool from said database to said processor by way of said communication channel;
   collecting said health data for at least one patient from said data source of a healthcare service provider;
   creating a record based on said health data, said record being created in a format used by a medical plan provider;
   transmitting said record from said processor to said database; and
   storing said record in said database in a location accessed by said medical plan provider.

11. The method of claim 10, further comprising the step of;
building a tool set that is used for the collection of specific health data.

12. The method of claim 11, further comprising the step of:
transmitting said tool set to said processor.

13. The method of claim 10, further comprising the step of:
authenticating an operator of said processor.

14. The method of claim 10, further comprising the step of:
executing said at least one tool on said processor.

15. The method of claim 12, further comprising the step of:
fetching an assignment based on authentication of said operator.

* * * * *